United States Patent [19]  [11] 4,016,265
Inoue et al.  [45] Apr. 5, 1977

[54] SYNERGISTIC INSECTICIDAL COMPOSITIONS CONTAINING β-EXOTOXIN

[75] Inventors: Tadahiko Inoue, Tokyo; Gosaburo Dowke, Shizuoka; Hideo Itoh, Shimizu, all of Japan

[73] Assignee: Sandoz, Inc., E. Hanover, N.J.

[22] Filed: Nov. 8, 1971

[21] Appl. No.: 196,809

[30] Foreign Application Priority Data
Nov. 14, 1970 Japan ............................. 45-100371

[52] U.S. Cl. ................................. 424/200; 424/203; 424/212; 424/222; 424/225; 424/245; 424/253

[51] Int. Cl.$^2$ ............................................. A01N 9/36

[58] Field of Search .......... 424/203, 200, 222, 212, 424/225, 115, 253

[56] References Cited

UNITED STATES PATENTS 3,087,865  4/1963  Drake et al. ........................ 195/96

OTHER PUBLICATIONS

Chemical Abstracts, 60:3434c (1964).

Pesticide Index–Frear– 4th Ed., pp. 139, 140, (1969) 183, 314 & 373.

*Primary Examiner*—Leonard Schenkman
*Attorney, Agent, or Firm*—Gerald D. Sharkin; Richard E. Vila

[57] ABSTRACT

A synergistic insecticidal composition comprises as a first ingredient the β-exotoxin of *Bacillus thuringiensis* or a metal salt thereof and has a second ingredient of one or more of the following chemical insecticides:

O,O-diethyl-O-(2-isopropyl-4-methyl-6-pyrimidyl) thionophosphate,

O,O-dimethyl, α,α,α-trichloro-1-hydroxyethyl phosphonate,

α-methoxy-4H-1,3,2-benzodioxaphosphorin-2-thione,

O,O,-dimethyl S-(α-(ethoxycarbonyl)benzyl) phosphorodithioate,

O,O-dimethyl S-(4-chlorophenyl) phosphorothioate

The first and second ingredients are used generally in a ratio of about 0.5:1 to 2.0:1 and may be dispersed in a major portion of an agronomically acceptable carrier.

12 Claims, No Drawings

SYNERGISTIC INSECTICIDAL COMPOSITIONS CONTAINING β-EXOTOXIN

BACKGROUND OF THE INVENTION

Organic phosphorous insecticides have appeared after the Second World War, playing the leading role in the eradication of hazardous insects. However, the disadvantages of these materials, such as development of insect resistance, the considerable toxicity of the material to humans and cattle, and simultaneous eradication of natural enemies, have been noticed in recent years. The most effective and widely used organic phosphorous insecticides are:

O,O-diethyl-O-(2-isopropyl-4-methyl-6-pyrimidyl)thionophosphate (referred to as Diazinon).

O,O-dimethyl, α,α,α-trichloro-1-hydroxyethyl phosphonate (referred to as DEP).

α-methoxy-4H-1,3,2-benzodioxaphosphorin-2-thione (referred to as Salithion).

O,O-dimethyl S-(α-(ethoxycarbonyl)benzyl)phosphorodithioate (referred to as PAP).

O,O-dimethyl S-(4-chlorophenyl) phosphorothioate (referred to as DMCP).

*Bacillus thuringiensis*, a spore forming microorganism with crystalline parasporal bodies, has been employed commercially as a microbial insecticide for the control of insects such as species of the order Lepidoptera and certain flies and mites. *B. thuringiensis* and its use as an insect pathogen is described inter alia, in C. L. Hannay and P. Fitz-James, "The Protein Crystals of *Bacillus thuringiensis* Berliner", Can. J. Microb., I, 694–710 (1955); A. M. Heimpel, "A Critical Review of *Bacillus thuringiensis* var. *thuringiensis* Berliner and Other Crystalliferous Bacteria", Ann. Rev. Entomology, 12, 287–322, (1967). *B. thuringiensis* insecticides are quite specific and are harmless to non-susceptible orders of insects, and relatively safe to animals and man.

"Endotoxin" is used by the art to define the toxicity associated with the water-insoluble crystals. "Exotoxin" denotes the so-called heat-stable, water-soluble fly toxin produced by *Bacillus thuringiensis* var. *thuringiensis* organisms. The water-soluble, heat-stable exotoxin was first reported in 1959 when its toxicity against the larvae of flies was noted. A review of the heat-stable exotoxin is contained in the previously mentioned article by A. M. Heimpel. This article summarizes the activity of the exotoxin (therein referred to as B.t. β-exotoxin) and concludes that exotoxin is effective against insects belonging to some species of the orders "Lepidoptera, Diptera, Hymenoptera, Coleoptera, and Orthoptera". It is also reported that exotoxin affects insects only at molting or during metamorphosis.

The probable chemical structure of *Bacillus thuringiensis* exotoxin has been elucidated by Bond et al., "A Purification and some Properties of an Insecticidal Exotoxin from *Bacillus thuringiensis* Berliner", R. P. M. Bond, C. B. C. Boyce and S. J. French, Biochem. J. (1969), 114, 477–488.

The proposed structure is:

Various processes are known for the production of exotoxin. All involve the fermentation of a *Bacillus thuringiensis* variety thuringiensis organism in a medium such as the following:

| Ingredient | Weight (%) |
|---|---|
| Cane Molasses | 0.5 |
| Beet Molasses | 0.5 |
| Cottonseed Oil Meal | 2.0 |
| Casein | 1.0 |
| Corn Steep Liquor | 3.33 |
| $CaCO_3$ | 0.1 |

The medium is adjusted to a pH of about 7.6 with ammonium hydroxide and then sterilized at about 120° C. for about 15 minutes. The medium is inoculated with *Bacillus thuringiensis* var. *thuringiensis* and the fermentation is conducted for about 24 hours at about 30° C. At the termination of the fermentation the cells in the broth are in the prespore stage of development and not more than about 1% of the total population contained spores.

The final whole culture is screened through a 200 mesh screen and the resulting mixture of cells and liquor is concentrated at about 125° F. with a vacuum of about 25 inches of mercury. Final drying and micropulverizing produced a 200 mesh powder which is characterized by a $LD_{50}$ of 2.9 mg%.

Another process for the production of both the exotoxin and endotoxin of *Bacillus thuringiensis* is proposed by Drake et al. U.S. Pat. No. 3,087,865. Drake et al. further disclose the precipitation of exotoxin from aqueous supernatant fermentation liquor by addition of calcium chloride. The calcium salt thus produced, as well as corresponding magnesium and barium salts, are disclosed to possess insecticidal activity.

Other salts of β-exotoxin which evidence insecticidal activity and may also be used in accordance with this invention are the copper, cadmium, manganese, tin, zinc, lead, cobalt, aluminum and iron salts.

DESCRIPTION OF THE INVENTION

The present invention proposes to minimize the untoward side effects of organophosphorous insecticides and reserving their prominent insecticidal activity. The present invention is based on unexpected findings of marked synergistic insecticidal activity obtained by the combination of β-exotoxin originated from *Bacillus thuringiensis* with the organophosphorous chemicals, Diazinon, DEP, Salithion, PAP and DMCP. The combination exerts its pesticidal activity at far smaller concentrations as compared with the dosage required in sole applications of the respective ingredients. In addition, the combined composition thus obtained is effective against insects which have acquired resistance to the organophosphorous insecticidal compounds.

The influence on the natural enemies of the target insects is substantially reduced. The synergistic insecticidal composition according to the present invention provides a unique means of eradicating hazardous insects in view of marked insecticidal activity combined with secondary factors such as low toxicity to the man and cattle, and less influence on the natural enemies.

Briefly, the compositions of this invention comprise a first ingredient of the group consisting of β-exotoxin and metal salts thereof and a second ingredient of the group consisting of O,O-diethyl-O-(2-isopropyl-4-methyl-6-pyrimidyl)-thionophosphate; O,O-dimethyl, α,α,α-trichloro-1-hydroxyethyl phosphonate; α-methoxy-4H-1,3,2-benzodioxaphosphorin-2-thione; O,O-dimethyl S-(α-(ethoxycarbonyl)benzyl) phosphorodithioate; and O,O-dimethyl S-(4-chlorophenyl) phosphorothioate. The invention also contemplates admixtures of the defined ingredients with an agronomically acceptable carrier, the total active ingredients comprising preferably about 1% to 40% of the admixture of active ingredients and carrier.

Exotoxin is known to possess insecticidal activity against the larvae of fly. However, the activity is quite weak or nil against certain other hazardous insects, and it is practically of no use in eradication of parasitic insects. Nevertheless, blending exotoxin with Diazinon, DEP, Salithion, PAP or DMCP results in a tremendous potential and prolonged action of the insecticidal activity.

The dosage and concentration of the insecticidal composition vary depending on the modes of application. In the case of powdery moth, green caterpillar, cabbage armyworm, and aphid, 200 to 800 liters per acre of a liquid preparation containing 50–250 ppm of the organophosphorous insecticide, and 100–500 ppm of β-exotoxin gives excellent protection which persists for 1–3 months after spraying. Sole application of Diazinon and the like requires spraying 200–800 liters per acre in a concentration of more than 500 ppm. In the compositions of this invention the proportion of organophosphorous insecticide to exotoxin is in the range of 0.1:1 to 10:1, and most preferably 0.5:1 to 2:1.

The insecticidal compositions according to the present invention exert a marked eradicating effect against a variety of hazardous insects and are particularly useful for eradication of those insects which are difficult to treat by organophosphorous insecticides alone.

For example, the powdery moth has been observed to increase in vegetable fields. Quick development of insecticide resistance and short life cycle render eradication extremely difficult. However, application of the insecticidal composition according to the present invention provides satisfactory and persisting results.

For the eradication of sanitary hazardous insects, a typical example is shown by the cockroach. This insect is found to increase in the urban districts and exhibit marked resistance to the organophosphorous insecticides. Though it is sensitive to chlorine-containing insecticides such as Dieldrin, use of these chlorine-containing insecticides may be limited in the near future in view of the residual toxicity problem.

The synergistic insecticidal compositions of this invention provide a key to the solution of this problem. For example, a poison diet containing 0.1% of Diazinon and 0.5% of exotoxin gives rise to an extremely high eradication effect on cockroach. The insecticidal effect is far superior to the diet containing only 0.1% of Diazinon. Furthermore, the insecticidal effect of the preparation containing 0.5% of exotoxin alone is nil.

The toxicity of exotoxin against warm blooded animals and fish is extremely low. In addition, the toxicity to insects is obtained via the oral route. Accordingly, the effects on the natural enemies of the hazardous insects are small compared with contact poisons such as BHC.

The synergistic effect of this invention does not exist in the case of other types of organophosphorous compounds, including EPN, Parathion, Methyl parathion, and the like. Chlorine-containing insecticides such as DDT, BHC, Endrin, and the like, are also unaffected by exotoxin.

The invention is illustrated by the following examples:

EXAMPLE 1

Test solutions in an amount of 30 ml. and having the concentrations specified in Table 1 were sprayed onto cabbage cultivated in porcelain pots 12 cm in diameter. After 24 hours, the leaf was cut and placed in a petri dish having a diameter of 12 cm and 10 tobacco cutworm larvae (third stage) were allowed to eat the treated cabbage leaf for three days. This was followed by feeding with a fresh untreated leaf. The mortality after 1, 3, 5, and 9 days was determined. The results of Table 1 are the average of three such experiments.

Table 1

| Test Preparation | Concentration (Active ingredient) ppm | Mortality after release of the insect | | | |
|---|---|---|---|---|---|
| | | 1 day | 3 days | 5 days | 9 days |
| Exotoxin alone | 1000 | 0 % | 5 % | 20 % | 65 % |
| | 500 | 0 | 5 | 20 | 60 |
| | 100 | 0 | 0 | 16 | 20 |
| | 50 | 0 | 0 | 5 | 20 |
| Diazinon alone | 100 | 28 | 44 | 47 | 47 |
| Diazinon + exotoxin | 100 + 100 | 100 | 100 | 100 | 100 |
| Diazinon + exotoxin | 100 + 200 | 100 | 100 | 100 | 100 |
| DEP alone | 100 | 9 | 14 | 18 | 32 |

Table 1-continued

| Test Preparation | Concentration (Active ingredient) ppm | Mortality after release of the insect | | | |
|---|---|---|---|---|---|
| | | 1 day | 3 days | 5 days | 9 days |
| DEP + exotoxin | 100 + 100 | 31 | 73 | 95 | 100 |
| DEP + exotoxin | 100 + 200 | 68 | 90 | 100 | 100 |
| DEP + exotoxin | 100 + 500 | 100 | 100 | 100 | 100 |
| Salithion alone | 100 | 33 | 33 | 35 | 35 |
| Salithion + exotoxin | 100 + 100 | 65 | 95 | 100 | 100 |
| Salithion + exotoxin | 100 + 200 | 100 | 100 | 100 | 100 |
| PAP alone | 100 | 42 | 53 | 58 | 63 |
| PAP + exotoxin | 100 + 100 | 100 | 100 | 100 | 100 |
| DMCP alone | 100 | 20 | 20 | 20 | 25 |
| DMCP + exotoxin | 100 + 500 | 100 | 100 | 100 | 100 |

EXAMPLE 2

Thirty ml. of each test solution at the specified concentrations was sprayed onto cabbage cultivated in a pot. The cabbage leaves were cut off periodically and placed in petri dishes of 9 cm in diameter. Ten young larvae of powdery moth were placed in each dish and the mortality determined after 24 hours. The results of Table 2 are the average of two replications.

Table 2

| Test Preparation | Concentration (ppm) | Mortality | | | |
|---|---|---|---|---|---|
| | | 1st day | 4 days after | 8 days after | 16 days after |
| Exotoxin alone | 200 | 10 % | 3 % | 0 % | 0 % |
| Diazinon alone | 100 | 36 | 5 | 0 | 0 |
| Diazinon + exotoxin | 100 + 200 | 100 | 100 | 100 | 95 |
| DEP alone | 100 | 20 | 0 | 0 | 0 |
| DEP + exotoxin | 100 + 200 | 100 | 100 | 76 | 43 |
| Salithion alone | 100 | 40 | 10 | 0 | 0 |
| Salithion + exotoxin | 100 + 200 | 100 | 100 | 100 | 63 |
| PAP alone | 100 | 65 | 20 | 0 | 0 |
| PAP + exotoxin | 100 + 200 | 100 | 100 | 100 | 100 |
| DMCP alone | 100 | 40 | 0 | 0 | 0 |
| DMCP + exotoxin | 100 + 200 | 100 | 100 | 100 | 20 |
| Control | | | | | |
| EPN | 100 | 50 | 40 | 20 | 0 |
| EPN + exotoxin | 100 + 200 | 62 | 55 | 43 | 0 |
| Parathion | 100 | 73 | 30 | 25 | 0 |
| Parathion + exotoxin | 100 + 200 | 50 | 60 | 20 | 0 |
| BHC | 500 | 80 | 40 | 45 | 20 |
| BHC + exotoxin | 500 + 500 | 88 | 50 | 30 | 0 |
| Non-treatment | — | 0 | 0 | 0 | 0 |

Diazinon, DEP, Salithion, PAP, and DMCP were found to be synergized by blending with exotoxin. A marked potentiation and improvement in residual effect with respect to the insecticidal activity against the young larvae of powdery moth are shown. Noticeable synergistic effect could not be observed upon blending exotoxin with EPN, parathion, BHC and the like.

EXAMPLE 3

Cabbage fields infested with powdery moth larvae were divided into separate areas of 3.3 square meters. Wettable powders containing 20% of exotoxin, emulsions containing 40% of Diazinon, and wettable powders containing 10% of exotoxin and 20% of Diazinon were diluted with water and sprayed in an amount of 300 ml. per area. The degree of dilution for each insecticide is shown in the table. The test was carried out in 3 replications, and the number of surviving insects was determined immediately prior to spraying and at 2, 6, 11, and 18 days after the spraying. The results are shown in Table 3.

Table 3

| Test preparation | Dilution degree times | Concentration (ppm) | Surviving powdery moth (mean value for 3 districts) Immediately before spraying | 2 days after | 6 days after | 11 days after | 18 days after |
|---|---|---|---|---|---|---|---|
| Exotoxin 20% wettable powder | 1,000 | 200 | 34.7 | 20.3 | 14.7 | 13.6 | 41.4 |
| Diazinon 40% emulsion | 2,000 | 200 | 24.0 | 0 | 18.3 | 28.0 | 67.3 |
| Exotoxin 10% diazinon 20% emulsion | 1,000 | 100 + 200 | 40.3 | 0 | 0 | 1.1 | 0 |
| Non- | | | | | | | |

Table 3-continued

| Test preparation | Dilution degree times | Concentration (ppm) | Surviving powdery moth (mean value for 3 districts) | | | | |
|---|---|---|---|---|---|---|---|
| | | | Immediately before spraying | 2 days after | 6 days after | 11 days after | 18 days after |
| spraying | — | — | 23.6 | 18.8 | 26.7 | 37.0 | 50.4 |

As seen from the above Table, the combination of exotoxin and Diazinon shows a very noticeable activity for preventing powdery moth larvae and such a combination apparently provides the synergistic activity as compared with the activity in the concentrations of the single uses.

EXAMPLE 4

In petri dishes of 9 cm diameter and 7 cm height were placed 200 g. of soybean cake medium mixed with the specified concentrations of test insecticide. Thirty third-stage fly larvae were placed in each dish and each dish was covered with gauze. After about 2 weeks, the total number of ecdyzed adult fly insects was determined. Each treatment was performed in 5 replications. The average of the results is shown in Table 4.

Table 4

| Test Insecticide | Concentration in the medium (ppm) | Number of larvae tested | Number of ecdyzed adult insect |
|---|---|---|---|
| Exotoxin | 20 | 150 | 61 |
| " | 10 | 150 | 79 |
| Diazinon | 20 | 150 | 63 |
| " | 10 | 150 | 72 |
| Diazinon + exotoxin | 10 + 10 | 150 | 0 |
| " | 5 + 5 | 150 | 0 |
| DEP | 20 | 150 | 43 |
| " | 10 | 150 | 81 |
| DEP + exotoxin | 10 + 10 | 150 | 0 |
| " | 5 + 5 | 150 | 0 |
| Salithion | 20 | 150 | 34 |
| " | 10 | 150 | 58 |
| Salithion + exotoxin | 10 + 10 | 150 | 0 |
| " | 5 + 5 | 150 | 0 |
| PAP | 20 | 150 | 24 |
| " | 10 | 150 | 50 |
| PAP + exotoxin | 10 + 10 | 150 | 0 |
| " | 5 + 5 | 150 | 0 |
| DMCP | 20 | 150 | 43 |
| " | 10 | 150 | 87 |
| DMCP + exotoxin | 10 + 10 | 150 | 0 |
| " | 5 + 5 | 150 | 0 |
| Control Parathion | 20 | 150 | 60 |
| " | 10 | 150 | 101 |
| Parathion + exotoxin | 10 + 10 | 150 | 111 |
| " | 5 + 5 | 150 | 93 |
| Methyl parathion | 20 | 150 | 41 |
| " | 10 | 150 | 93 |
| Methyl parathion + exotoxin | 10 + 10 | 150 | 70 |
| " | 5 + 5 | 150 | 94 |
| EPN | 20 | 150 | 23 |
| " | 10 | 150 | 64 |
| EPN + exotoxin | 10 + 10 | 150 | 44 |
| " | 5 + 5 | 150 | 58 |
| Non-treatment | — | 150 | 99 |

EXAMPLE 5

The bottom of petri dishes of 9 cm diameter, 7 cm height, was covered with filter paper. Smaller petri dishes of 3 cm diameter and containing 10 ml of test solutions diluted with milk to specified concentration, were placed on the large dishes. Five adult brown winged aphids were released in each dish which was then covered with a cover glass having an opening for air and allowed to stand at 25° C. for five days. Mortality was then determined. Each treatment was done with four replications. Average results are set forth in Table 5.

Table 5

| | Concentraton (%) | Number of insects tested | Mortality after 5 days |
|---|---|---|---|
| Exotoxin | 1.0 | 20 | 0 % |
| Diazinon | 0.1 | 20 | 25 |
| Diazinon + exotoxin | 0.1 + 0.5 | 20 | 95 |
| " | 0.2 + 0.5 | 20 | 100 |
| " | 0.2 + 0.1 | 20 | 100 |
| DEP | 0.1 | 20 | 10 |
| DEP + exotoxin | 0.1 + 0.5 | 20 | 85 |
| " | 0.2 + 0.5 | 20 | 100 |
| " | 0.2 + 1.0 | 20 | 100 |

The insecticidal composition of this invention can be prepared in the form of dust, wettable powder, emulsion, granule, or aqueous solution by blending the active ingredients with a suitable carried and, if desired, adding a surfactant, dispersing agent, spreader, or the like.

The present invention is further illustrated in detail by the following examples.

EXAMPLE 6

A. Exotoxin 15%, Diazinon 25%, white carbon 10%, clay 46.5%, sodium lignin sulfonate 1.5%, and sodium alkyl aryl sulfonate 1.5%, were mixed uniformly and pulverized to provide a wettable powder.

B. Exotoxin 20%, DEP 10%, methanol 30%, and dimethyl sulfoxide 30% were dissolved in polyoxy-ethylene alkyl ether.

C. Exotoxin 2%, Salithion 1%, clay (-300 mesh) 96%, and white carbon 1% were blended uniformly and subsequently pulverized to provide a dust.

D. Commercial cornstarch 44.4%, carboxymethyl cellulose 5%, starch 50%, exotoxin 0.5%, and Diazinon 0.1% were blended uniformly, kneaded after addition of water to make a dough, extruded through 5 cm.- holes, and dried and cut into 5 – 10 cm. lengths.

What is claimed is:

1. An insecticidal composition consisting essentially of a first ingredient selected from the group consisting of β-exotoxin and metal salts thereof and a second ingredient selected from the group consisting of O,O-diethyl-O-(2-isopropyl-4-methyl-6-pyrimidyl)-thionophosphate; O,O-dimethyl, α,α,α-trichloro-1-hydroxyethyl phosphonate; α-methoxy-4H-1,3,2-benzodioxaphosphorin-2-thione; O,O-dimethyl S-(α-(ethoxycarbonyl)benzyl) phosphorodithioate; and O,O-dimethyl S-(4-chlorophenyl) phosphorothioate; said first and second ingredients being present in the ratio of about 0.1:1 to about 10:1 by weight.

2. The composition of claim 1 in which said second ingredient is O,O-diethyl O-(2-isopropyl-4-methyl-6-pyrimidyl)-thionophosphate; and said first and second ingredients are present in the ratio of about 0.5:1 to about 2.0:1.

3. The composition of claim 1 in which said second ingredient is O,O-dimethyl, α,α,α-trichloro-1-hydroxyethyl phosphonate; and said first and second ingredients are present in the ratio of about 0.5:1 to about 2.0:1.

4. The composition of claim 1 in which said second ingredient is α-methoxy-4H-1,3,2-benzodioxaphosphorin-2-thione; and said first and second ingredients are present in the ratio of about 0.5:1 to about 2.0:1.

5. The composition of claim 1 in which said second ingredient is O,O-dimethyl S-(α-(ethoxycarbonyl)benzyl)phosphorodithioate; and said first and second ingredients are present in the ratio of about 0.5:1 to about 2.0:1.

6. The composition of claim 1 in which said second ingredient is O,O-dimethyl S-(4-chlorophenyl)phosphorothioate; and said first and second ingredients are present in the ratio of about 0.5:1 to about 2.0:1.

7. An insecticidal composition comprising a major portion of an agronomically acceptable carrier and about 1.0% to about 40%, based upon the weight of said composition, of active ingredients consisting essentially of a first ingredient selected from the group consisting of β-exotoxin and metal salts thereof and a second ingredient selected from the group consisting of O,O-diethyl-O-(2-isopropyl-4-methyl-6-pyrimidyl)-thionophosphate; O,O-dimethyl, α,α,α-trichloro-1-hydroxyethyl phosphonate; α-methoxy-4H-1,3,2-benzodioxaphosphorin-2-thione; O,O-dimethyl S-(α-(ethoxycarbonyl)benzyl) phosphorodithioate; and O,O-dimethyl S-(4-chlorophenyl) phosphorothioate; said first and second ingredients are present in the ratio of about 0.1:1 to about 10.0:1.

8. The composition of claim 7 in which said second ingredient is O,O-diethyl-O-(2-isopropyl-4-methyl-6-pyrimidyl) thionophosphate; said first and second ingredients are present in the ratio of about 0.5:1 to about 2.0:1.

9. The composition of claim 7 in which said second ingredient is O,O-dimethyl, α,α,α-trichloro-1-hydroxyethyl phosphonate; said first and second ingredients are present in the ratio of about 0.5:1 to about 2.0:1.

10. The composition of claim 7 in which said second ingredient is α-methoxy-4H-1,3,2-benzodioxaphosphorin-2-thione; said first and second ingredients are present in the ratio of about 0.5:1 to about 2.0:1.

11. The composition of claim 7 in which said second ingredient is O,O-dimethyl S-(α-(ethoxycarbonyl)benzyl) phosphorodithioate; said first and second ingredients are present in the ratio of about 0.5:1 to about 2.0:1.

12. The composition of claim 7 in which said second ingredient is O,O-dimethyl S-(4-chlorophenyl) phosphorothioate; said first and second ingredients are present in the ratio of about 0.5:1 to about 2.0:1.

* * * * *